United States Patent [19]

Collings et al.

[11] Patent Number: 5,073,753
[45] Date of Patent: Dec. 17, 1991

[54] HYDROCARBON FLAME IONIZATION DETECTOR

[75] Inventors: Nicholas Collings; Steven Dinsdale; Jonathan Willey, all of Cambridge, England

[73] Assignee: Cambustion, Limited, England

[21] Appl. No.: 460,869

[22] PCT Filed: Jul. 28, 1988

[86] PCT No.: PCT/GB88/00618
§ 371 Date: Feb. 1, 1990
§ 102(e) Date: Feb. 1, 1990

[87] PCT Pub. No.: WO89/01149
PCT Pub. Date: Feb. 9, 1989

[30] Foreign Application Priority Data

Aug. 3, 1987 [GB] United Kingdom ............... 8718332
Sep. 14, 1987 [GB] United Kingdom ............... 8721542
Oct. 27, 1987 [GB] United Kingdom ............... 8725093

[51] Int. Cl.⁵ .......................................... G01N 27/62
[52] U.S. Cl. ................................... 324/468; 324/464; 422/54; 436/154
[58] Field of Search ............... 324/464, 468, 470, 467; 340/632, 633; 422/54; 436/154

[56] References Cited

U.S. PATENT DOCUMENTS

| | | | |
|---|---|---|---|
| 3,690,146 | 9/1972 | Hofmann | 324/464 X |
| 3,762,878 | 10/1973 | Villalobos | 436/154 X |
| 4,182,740 | 1/1980 | Hartmann et al. | 436/154 X |
| 4,211,746 | 7/1980 | Mees | 422/54 |
| 4,264,817 | 4/1981 | Neukermans et al. | 324/470 X |
| 4,273,558 | 6/1981 | Nelson | 436/154 |
| 4,410,854 | 10/1983 | Kroneisen et al. | 324/468 |
| 4,508,685 | 4/1985 | Sisti et al. | 324/470 X |
| 4,524,047 | 6/1985 | Patterson | 324/468 X |
| 4,565,969 | 1/1986 | Olson et al. | 324/468 |

Primary Examiner—Kenneth A. Wieder
Assistant Examiner—Robert W. Mueller
Attorney, Agent, or Firm—Andrus, Sceales, Starke & Sawall

[57] ABSTRACT

A flame ionization detector comprises a housing forming a flame chamber for burning a mixture of hydrogen, oxidant and a sample gas. The flame chamber includes: a nozzle in which the sample gas and hydrogen are intimately mixed prior to injection, an igniter for igniting the gas emitted from the nozzle, inlets for hydrogen and oxidant, and an exhaust outlet through which the burnt gases are removed. A collector electrode is electrically insulated from the housing of the flame chamber. The nozzle and flame chamber housing are electrically grounded, and the collector electrode is maintained at a predetermined potential relative to ground. A pre-chamber is disposed adjacent to the flame chamber to provide a substantially constant pressure input of the sample gas to the nozzle.

9 Claims, 6 Drawing Sheets

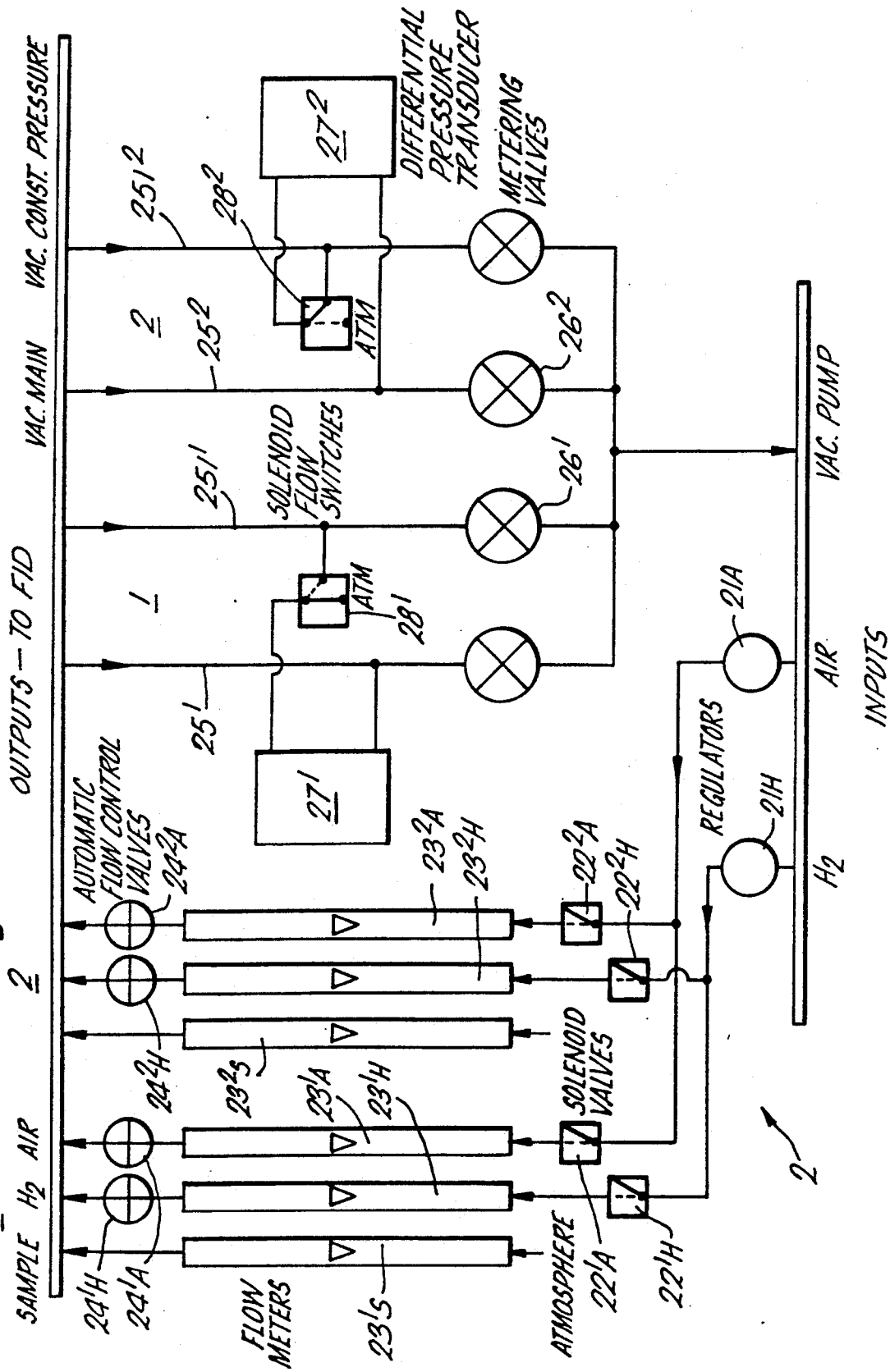
Fig. 2. GAS MANAGEMENT SYSTEM

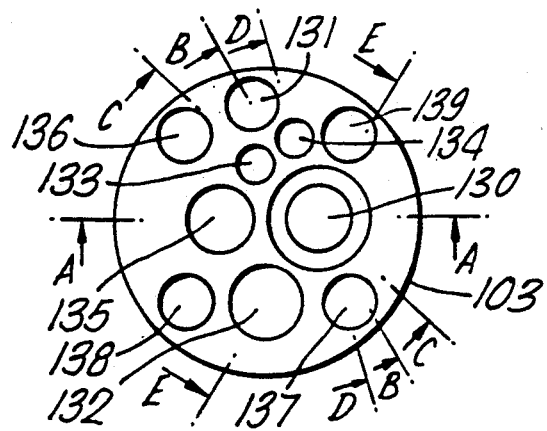
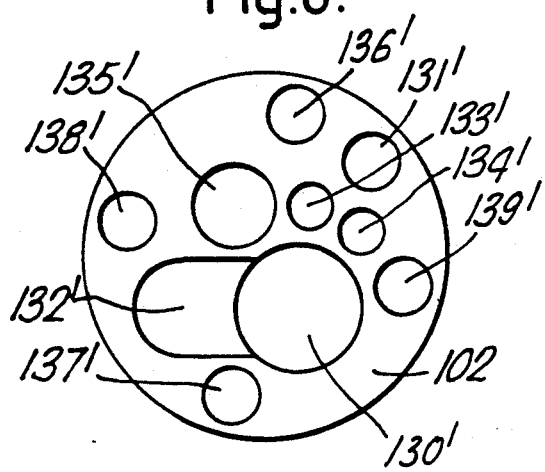
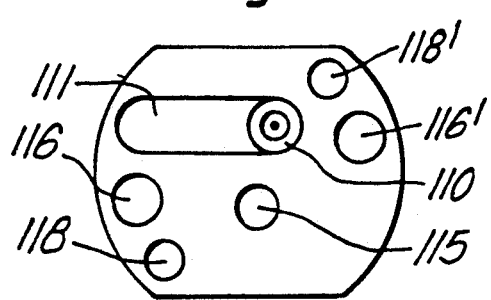
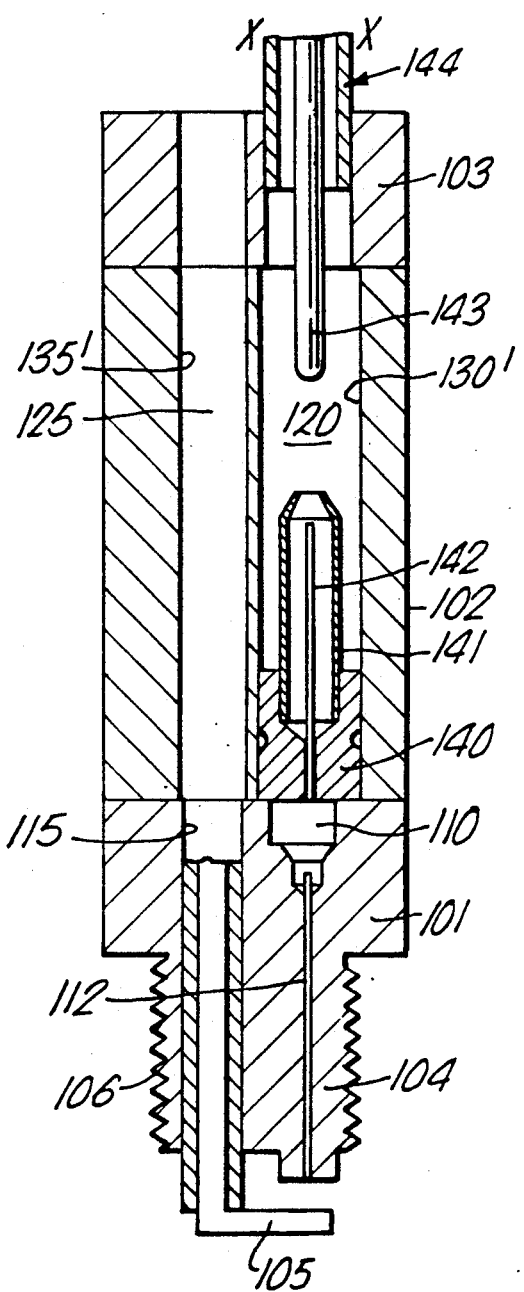

HYDROCARBON FLAME IONIZATION DETECTOR

The present invention relates to the detection of fuel concentration and unburnt hydrocarbons associated with combustion processes, in particular, a hydrocarbon flame ionization detector for the measurement of such parameters in internal combustion engines.

Meeting the stringent emissions legislation that exists in many countries requires very careful engine design. With the additional desirability of good fuel economy, new methods of examining the management of fuel within the combustion process are of great importance.

During the combustion of hydrocarbon (HC) fuels ions are produced to the extent of-about 1 ion pair for every $10^6$ carbon atoms in the fuel The level of ionization is sufficient for detection and forms the basis of the well-known flame ionization detector (FID) which is used almost universally for the routine measurement and legislative assessment of HC emissions from vehicles.

In an FID a sample of the gas under study is burnt in a hydrogen flame and the resulting ions are collected by means of an electrically biased electrode. The current in the electrode is found to be nearly exactly proportional to the rate of supply of HC molecules to the flame. The hydrogen flame is supported by an oxidant, normally air, the hydrogen flame itself producing negligible ionization. Mixtures of hydrogen and buffer gases (typically helium or nitrogen) are often used as the fuel gas for the FID, and in this specification, the term hydrogen will be used for simplicity when referring to the fuel gas as a mixture or just hydrogen.

Although conventional FID's work well, they have a drawback if rapid response is required, since they conventionally have a time constant of in the order of 1 second. This is due to the fact that the sample is led through a long tube from the sample origin (typically an engine exhaust) to the detector unit which may be several metres away. Diffusion processes in the sampling system then result in the poor time constant. In 1980 J. E. Fackrell published a paper (see J.Phys. E. Sci. Instru., Vol 13, 1980) showing how the basic frequency response could be improved dramatically by using a very short sample line, and by introducing the sample right at the tip of the burner within the FID chamber. In this way frequency responses of up to 300 Hz were achieved.

In Fackrell's design the flow of hydrocarbons into the FID chamber is proportional to the pressure difference between the pressure in the chamber and that in the surrounding atmosphere. Thus the measurement of hydrocarbon concentration is dependent on a steady ambient pressure at the sample point.

Fackrell's modification to the conventional FID is thus only suitable for use in constant pressure environments, and is unsuitable for use effectively for internal combustion engine studies, since, in all cases, the source of the hydrocarbons under study experiences considerable pressure fluctuations In addition, the design of the FID used by Fackrell does not embody certain improvements made possible by modern electronics and is of a more complex mechanical design than necessary as a result.

The present invention relates to a system for obtaining high frequency response measurements from sources with pressure fluctuations, and to improvements over existing designs of FID chambers.

According to the present invention there is provided a flame ionization detector comprising a housing forming a flame chamber for burning hydrogen, an oxidant, and a sample gas; the flame chamber including a nozzle at the tip of which the mixture of gases is burned; means for igniting the gas emitted from the nozzle; inlets for hydrogen and oxidant; an exhaust outlet through which the products of combustion are removed; a collector electrode electrically insulated from the housing of the flame chamber; the nozzle and flame chamber housing being electrically grounded and the collector electrode, in use, being maintained at a predetermined potential relative to ground; and pre-chamber means adjacent to the flame chamber for maintaining the pressure of the sampled gas supplied to the nozzle substantially constant.

Since the pressure at the point at which the fractional sample is removed is at a substantially constant pressure, the flow into the flame chamber is constant, the constant pressure environment being set by a connection to, say, a port of the pre-chamber.

The flame ionization detector of the invention may include a flame ionization detector wherein the pre-chamber has an input for sampled gas; a control port by means of which the pressure in the pre-chamber may be controlled; and a sampling output disposed transverse to the input and directly connected to the nozzle in the flame chamber, the arrangement being such that the sampled gas enters the sampling output substantially at the pre-chamber pressure.

Alternatively, the pre-chamber may have an input for sampled gas opening into the pre-chamber through a diffuser section to reduce dynamic pressure variations, the diffuser section having a relatively large open surface area to enable the maintenance in use of a substantially constant static pressure; a control port by means of which the pressure in the pre-chamber may be controlled; and a sampling output directly connected to the nozzle in the flame chamber.

The design of the junction, within the pre-chamber, between the sample flow and the flow into the flame chamber, may take various different forms. In one form the junction may take the form of a 'T' piece in which the source sample flows along one side of the top of the 'T' and the flame chamber flow is at right angles to it along the leg of the 'T', the 'T' being open at the intersection, on the other side of the top, so that the pressure therein is the same as that in the surrounding pre-chamber. In a second form, as a diffuser, the incoming source flow is led through a divergent duct or series of ducts to reduce flow velocity sufficiently to cut fluctuations in the dynamic head to negligible levels, a fractional flow being fed to the flame chamber substantially at constant pressure.

The pre-chamber may be connected to the sample source by means of a simple sample tube and the source may be the inlet or exhaust manifold of an engine, or the engine cylinder itself. If the fuel is a liquid such as petrol or diesel fuel, then a heated sample line may be required.

Depending on the sample being analysed and the requirements of the particular detection method used, the pre-chamber may be operated above or below atmospheric pressure, when operated below atmospheric pressure, the output being a vacuum output and air being bled in through an air input via a needle valve for example. When operating super-atmospherically the output may be bled through a needle valve.

Air is preferably bled into or out of the pre-chamber at a much greater rate than that at which the sampled gas is fed into the chamber, whereby pressure fluctuations from the sampled gas have a negligible effect on the pressure within the pre-chamber thus enabling constant pressure sampling to be achieved, increasing the accuracy of the FID.

The invention also includes a method of detecting hydrocarbon ionization using a detector as herein described.

Depending on the operational requirements of the process in any particular case and the polarity of the ions to be detected, the potential of the collector may be arranged to be negative or positive.

With this simple construction, which avoids the need for complex insulation between the nozzle and the housing and which also avoids the need for the polarizing electrode and its associated contacts and terminal clip etc., a low impedance input stage, analagous to a "virtual earth" input can be used as the input stage of the electronic signal processing unit that is required to process the electrical signal from the collector electrode, an isolation amplifier being utilized to allow the input stage to be biased above or below ground as required. Furthermore, the simple form of the flame chamber enables it to be shaped internally in a single boring operation, thus reducing manufacturing costs.

When sampling from an engine cylinder, a special access point may be provided or, preferably, a modified spark plug may be used, where the sample is taken by means of a small capillary tube in the body or centre electrode of the plug. The sampling tube may be located within a further tube which is fixed within the bore. By this means an effective seal between the bore and the sampling tube can be produced, the bore being drilled with a fine drill and the further tube soldered, brazed or otherwise permanently fixed in position within the bore, the sampling tube being removable when desired.

Thus, in-cylinder sampling may be achieved without engine modification, allowing the flame ionisation detector to be used to monitor concentrations in any engine at will.

To obtain a better frequency response, a special flame chamber and constant pressure pre-chamber may be provided in a re-designed spark plug.

Accordingly, therefore, there is provided, in combination within a common housing, a spark plug having a pair of HT electrodes between which a spark is generated for igniting a combustible gas; and a flame ionization detector of a type described above for measuring concentration of ions in the gas, a sampling tube being provided through the casing from a position adjacent to or at the surface of one of the HT electrodes, or through the spark plug body, to a mixing nozzle through which a mixture of the sampled gas and hydrogen are mixed prior to injection into a flame chamber of the FID in which the mixture is burnt and ion concentration measured.

This improves the transit time of the sampled gas and also the time constant of the detection system.

In this embodiment, the device preferably has a substantially conventional pair of HT electrodes, one overlying the other which is provided generally centrally or offset from the centre at one end of the device, but advantageously the centre or offset electrode is integrally formed with at least a base portion of the casing of the device and is therefore grounded in use and the other HT electrode is electrically insulated from the casing. By this means the mixing nozzle, the centre/offset HT electrode and the casing are all electrically grounded and it is only necessary to provide insulated connections for the other HT electrode and the collector electrode of the FID. This considerably simplifies construction of the device.

Preferably, the device is generally cylindrically formed from a plurality of casing or body sections which may be separated for maintenance or for installation of the device as required. The preferred arrangement is for the HT electrodes and an elongate bore through which the sampling gas passes in use to be provided in a base portion, the base portion including a screw threaded protrusion of appropriate dimensions for mounting the base portion in the screw threaded aperture which is conventional in an internal combustion engine cylinder head; a second, body, portion, containing the nozzle and flame chamber being attached to the base portion; and a closure cap containing the necessary connectors for HT current, hydrogen, oxidant etc. fitting on the end of the body portion remote from the base.

Preferably, as mentioned above, a narrow bore sampling tube is located within a tube fixed within the bore in the base portion of the device, thus allowing the sampling tube to be removable when the body portion is separated from the base.

The modular form of construction also facilitates mounting of the device in a cylinder head, particularly where the spark plug fixing aperture is provided at the base of a long and relatively narrow passage as is the case with many modern cylinder head designs. Furthermore, the modular construction enables base portions of different configurations (for example to suit different thread forms in cylinder heads) to be attached to the same body and cap portions thus reducing the number of separate items required to be manufactured.

Preferably, the sampling tube opens to a constant pressure chamber, which may be of the 'T' or divergent diffuser type. The pressure in the pre-chamber can be adjusted via a port in the casing and the closed environment of the device enables the pressure in the diffuser to be raised during non-use of the FID thus providing a net flow of gas out of the tip of the plug into the engine during this time and keeping the sampling tube free of deposits. When required the pressure can be switched to that required for sampling and thus protection for the sampling tube is readily provided by what may be termed a "pressure protect" system.

Furthermore, it may be required to operate the unit at various pressures (or vacuums for analysis of hydrocarbons at inlet conditions) and this can be achieved in the same way.

If a diffuser type of constant pressure system is employed it may be formed by a plurality of concentric close fitting tubes to provide a stepped divergent diffuser chamber The manufacture of a true conical diffuser section when the dimensions of the sampling tube are very small (sub-millimetre) may be difficult and plural concentric tubes provide substantially the same desired diffusion effect. However, a conical diffuser is possible and may be provided if required.

In the tight confines of the sparking plug embodiment of the FID and constant pressure system, a diffuser type of constant pressure system may be preferred, but the 'T' type may generally have better performance, and may thus be preferred in some designs.

The detector also has applications in the investigation of droplet/vapour pressure in combustion chambers as well as being capable of use in determination of hydrocarbon quench layers (the build-up of unburnt hydrocarbons on cold surfaces in i/c engines due to vapour being condensed onto the walls) etc.

The FID may also be used with particular advantage, via the sampling systems described, or simply by sampling from a vent in the exhaust system, to characterize the cold start behaviour of diesel engines since the FID will be much more highly sensitive to the "white smoke" (unburnt, vapourised fuel) conditions than to black and blue smoke conditions.

It is preferable to be able to purge the vacuum line and vapour trap of hydrocarbon containing gas, and this may be achieved by fitting a non-return valve between the condensate bowl and atmosphere, the valve remaining closed under normal operation, but being opened by switching the air supply into the vacuum line at the control box to purge the line and bowl.

Examples of apparatus constructed in accordance with the invention will now be described with reference to the accompanying drawings in which:

FIG. 2 is a diagram of a gas management system of the apparatus;

FIGS. 5 to 13 show various views of a combined spark plug and FID with constant pressure chamber, in which the diffuser type of pre-chamber is implemented;

FIG. 5 is a plan view of a cap portion of a spark plug and a flame ionization detector in combination within a common housing;

FIG. 6 is a plan view of a body portion;

FIG. 7 is a plan view of the base portion;

FIG. 8 is a longitudinal section on A—A in FIG. 5;

FIG. 9 is a section on B—B in FIG. 5;

FIG. 10 is a section on C—C in FIG. 5;

FIG. 11 is a composite of partial sections on D—D and E—E in FIG. 5;

FIG. 12 shows an enlarged view of a connector for the vacuum line and collector electrode; and FIG. 13 is an enlarged view of a thermocouple/glow plug unit of the device.

Figure 3:
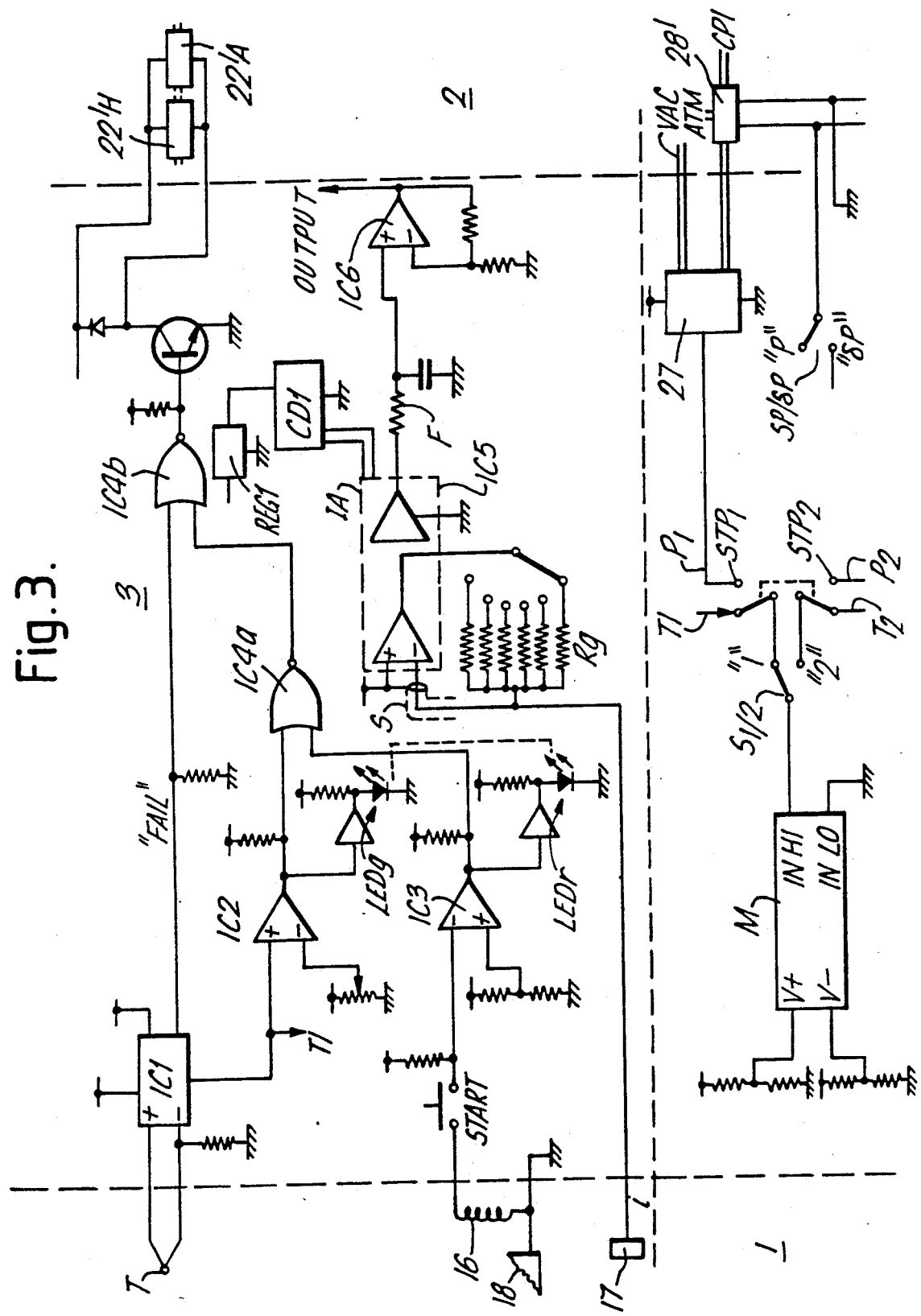
FIG. 3 is a simplified schematic of the signal processing/control circuit.
Figure 9:
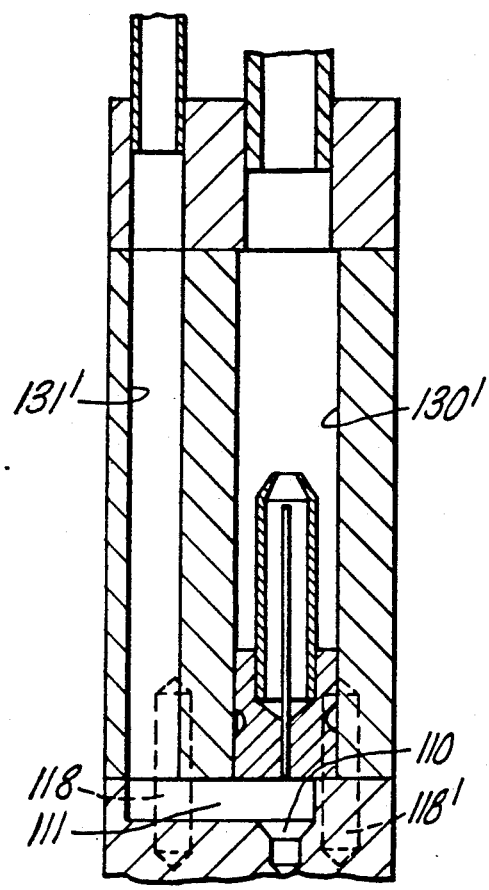
Figure 10:
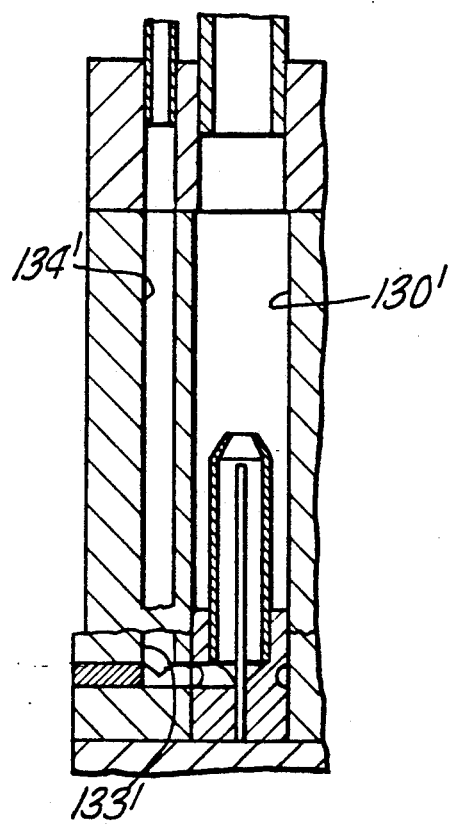
Figure 11:
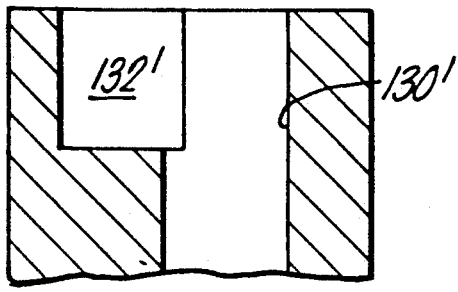
Figure 12:
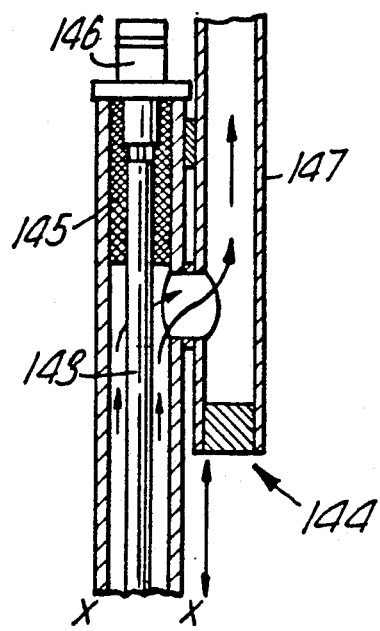
Figure 13:
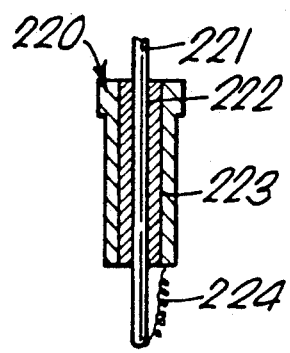

A flame ionization detector according to the present invention provides real time HC concentration analysis and consists of three main parts, a gas sampling head and constant pressure system 1 (FIG. 1A or FIG. 1B) a gas management system 2 (FIG. 2), and an electronic signal processing, control unit 3 (FIG. 3). The sample gas is inputted to the sampling head through a short capillary tube 10, through the constant pressure sampling device 4, and is introduced at the tip of the nozzle 11 with hydrogen or a hydrogen/helium or a hydrogen/nitrogen mixture fed through line 12. Compressed air is fed to the sampling head 1 through line 13 and the flow rates of air and hydrogen are controlled by the gas management system 2. Burnt gases are extracted through outlet 14 by an adjustable vacuum supply which controls the flow rate of the sample. The adjustable vacuum supply preferably includes a condensate trap to reduce or eliminate condensate flow through the vacuum supply. This may comprise a body housing a sintered metal filter which acts as both a flame trap and as a condensate trap and air may be bled controllably to the vacuum path at a location immediately after the trap. By this means the relative humidity in the vacuum line can be decreased and the chance of condensation in it reduced. A tapping (not shown in FIG. 1A or 1B) for a thermocouple T (see FIG. 3) is also provided at the level of the exhaust outlet 14.

In the gas sampling head 1 a hydrogen flame is caused to burn in the flame chamber 15, the flame being ignited by a glow plug 16 and the flame tip being arranged in close proximity to a collector electrode 17 which is biased, in use, by the signal processing/control unit 3 at a positive potential of 180 V. The collector electrode is electrically insulated from the housing 18 by a connector assembly 19 which includes a PTFE insulator 19'. The nozzle 11 and sampling head housing 18 are held at ground potential. Combustion of any HC present in the sample results in ionization which is collected by the collector electrode 17 which in turn results in a current flow which is amplified by the signal processing/control unit 3 to provide an output signal which is proportional to the measured ionization current and thus to the HC concentration in the sampled gas.

This example unit has two sampling heads 1 (of either FIG. 1A or FIG. 1B type) and the gas management system 2 therefore has two sections, one for each head. Hydrogen mixture and air are supplied from conventional gas bottles (not shown) and are fed through appropriate couplings (not shown) through regulators 21A, 21H to solenoid controlled input valves $22^1A, 22^1H, 22phu 2A, 22^2H$. The hydrogen, air and sample gas are all fed through respective rotameter-type flow meters $23^1H, 23^1A, 23^1S, 23^2H, 23^2A, 23^2S$ and the hydrogen and air are passed through automatic flow control valves $24^1H, 24^1A, 24^2H, 24^2A$ in order to maintain constant flow rates. The regulators 21 supply gas at a fixed 2 bar to prevent the upper pressure limit on the solenoid valves being approached. The automatic flow control valves 24 are designed to control, very accurately, very low flow rates against varying downstream back pressure and allow, with the aid of the flowmeters 23, accurate setting of the hydrogen and air inputs to the sampling head 1. The sample gas is also preferably controlled as regards pressure by the constant pressure sampling device 4.

After passing into the respective sampling head and being burnt therein, the gases are returned through a main vacuum supply line $25^1, 25^2$ through a metering valve $26^1 26^2$ and hence to atmosphere by means of a vacuum pump (not shown). By means of a differential pressure transducer $27^1, 27^2$ and solenoid controlled flow switches $28^1, 28^2$ a constant, but adjustable, vacuum pressure can be maintained in lines $25^1_1, 25^1_2$ and in the constant pressure sampling device 4.

The signal processing/control unit 3 shown in FIG. 3 performs conversion of the collector current i into an output voltage for each of the two sampling heads. It also contains conversion circuitry and logic circuitry necessary to control the gas supply based on information provided through appropriate sensors. The circuitry for only one of the channels CH1 is shown as they are identical.

The control system is designed to facilitate easy lighting and use of the FID and to provide a shut-off system if the flame in the flame chamber goes out. This prevents a build up of flammable gas.

The operating procedure is as follows. At start-up when the FID is unlit, a status indicator is off and the gas valves 22 are closed. Pressing the START button for the appropriate channel (1 or 2) will allow gas to flow only if the sampling head 1 is plugged in and the glow plug 16 is drawing current. Pushing the START button allows current to flow through the glow plug causing input to IC3 to drop to 2 volts if the glow plug is functioning. At this point the status indicator turns red by $LED_r$ being lit.

IC4a output is low if IC2 output or IC3 output is high and IC4b turns on an output transistor to open the appropriate solenoid valves in the gas supply 2, providing the FAIL output of IC1 is also low. A thermocouple T in chamber 15 provides an input to IC1.

Holding the START button in causes the FID to light and the temperature in chamber 15 steadily rises until it exceeds a pre-set threshold. This is sensed by the thermocouple sensor T in the sampling chamber 15 and the status indicator then turns amber by $LED_g$ being lit. After this occurs the START button may be released. Releasing the START button early before the status indicator turns amber returns the system to the initial start-up point and the start-up procedure has to be repeated.

On release of the START button after the temperature has reached the required threshold value, U the status indicator turns green, by $LED_r$ going out, to indicate proper and steady state functioning, but if the flame goes out and the temperature drops below the threshold the gas supply is caused to cut off and the unit again returns to its initial condition. The temperature signal from the thermocouple T is amplified by IC1 and if the thermocouple circuit is broken a fail output is provided so as to detect if the sampling head is plugged into the unit. Comparator IC2 has an output which is high when the temperature within the flame chamber 15 is detected as being greater than the threshold temperature thus lighting the appropriate indicator.

The loss of power to the unit is arranged to cause shut down of the procedure and of all the control valves which supply gas to the various sections of the unit.

The unit includes a digital meter M provided to measure both temperature and pressure by actuation of switches $STP_1, STP_2$ to switch the meter between temperature and pressure measuring positions and a further switch $S_1$ selects whether channel 1 or channel 2 is being monitored. Another switch $S_P/\delta P$ is provided to control the solenoid flow switches to measure depression P in the FID chamber or the pressure difference $\delta P$ between the FID chamber and the constant pressure sampling chambers. Each channel has identical control/signal circuitry.

When the system is operating the signal processing/control unit uses a low impedance input stage which senses the collector current i and gives an output voltage of i.Rg (Rg being the gain setting resistor). By using an isolation amplifier IA (which includes IC5 and which is driven by clock driver CD1) this input stage can be made to sit at a potential of 180 V above ground, thus providing the necessary collector bias. The collector cable is guarded by a 180 V shield S to minimize noise and also current leakage The signal is further amplified by IC6 by a factor of 10 and a filter F in front of IC6 removes the 25 kHz ripple caused by the modulation frequency of the isolation amplifier IA.

The output of IC6 provides the signal output which is fed to an oscilloscope or other display device to provide an indication of detected ionization levels. As the system is real time and has a frequency response in excess of 300 Hz an oscilloscope or similar display device is necessary for analysis of the output. If desired the oscilloscope or other display device may be incorporated into the apparatus.

The constant pressure sampling device 4 is mounted directly below the FID sampling head 1 and in the FIG. 1A example has a housing 40 providing a pre-chamber 41, a capillary output 10 to the nozzle 11 in the sampling head, and a vacuum output 44, supplied from the gas management system 2, the sample gas being fed in through the fitting 46 by a stainless steel capillary tube 45. The capillary 10 to the FID nozzle extends substantially perpendicularly from the capillary tube 45 and in use maintenance of a constant pressure within the pre-chamber 41 by control of the vacuum output 44 ensures that the jet has a constant static pressure and thus that the fractional sample bled off from the sample entering the pre-chamber 41 also has a constant pressure. This ensures consistency of mass flow rate of the hydrocarbon sample.

Figure 1A:
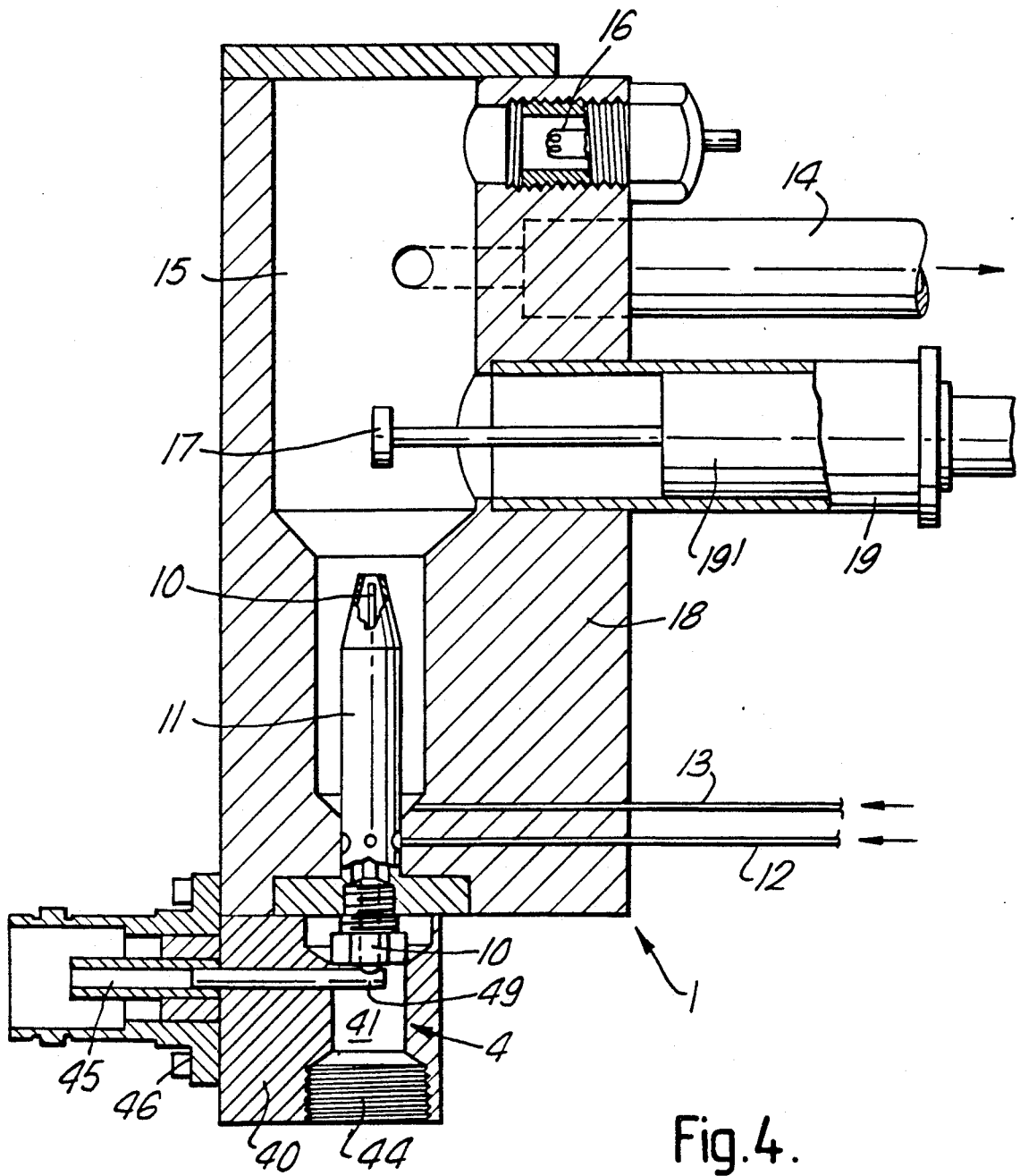
FIG. 1A is a diagrammatic partially-sectioned view of the sensor module of an FID apparatus showing a first type of constant pressure chamber.
Figure 4:
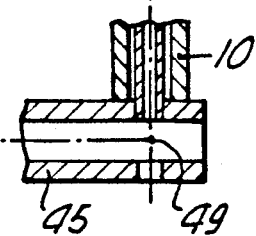
FIG. 4 shows detail of the pre-chamber of FIG. 1A.
Figure 1B:
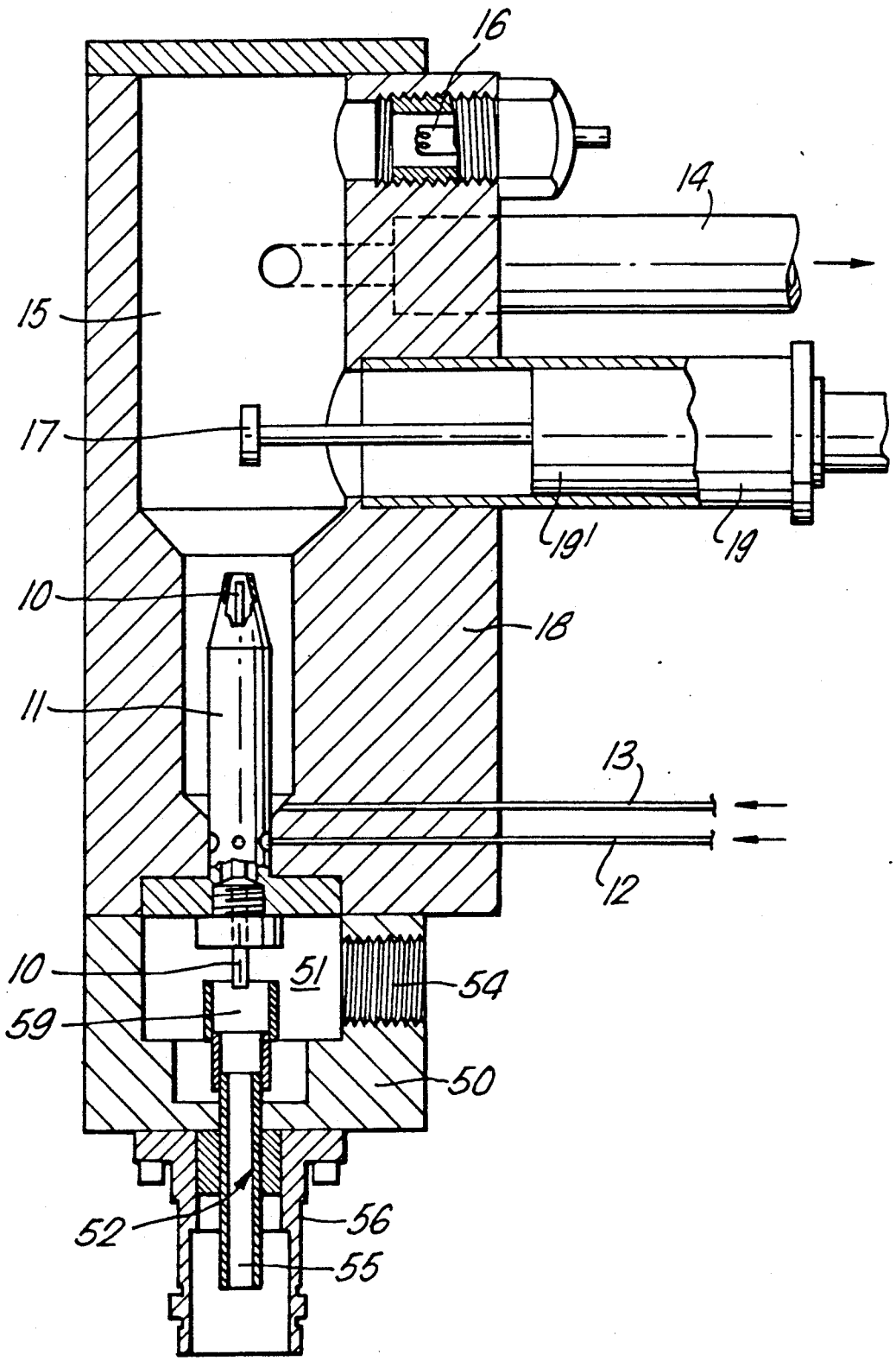
FIG. 1B is a diagrammatic partially-sectioned view of the sensor module of an FID apparatus showing a second type of constant pressure chamber.

FIG. 1B shows an alternative construction to that of FIG. 1A, in which the pre-chamber has a housing which contains a diffuser 52. The sampled gas arriving from the sampling tube 55 in connection 56 is diffused to low velocity until, at the exit 59 of the diffuser 52, the velocities are low enough to have an acceptably small dynamic head and cause a negligible flow variation in the flame chamber capillary 10. The flow along the capillary 10 is thus controlled by the difference between the flame chamber pressure and the pressure in the diffuser chamber, the latter being controlled via a port 54.

A combination of a spark plug and a flame ionization detector within a common housing is shown in FIGS. 5 to 13.

The device has a generally cylindrical overall shape and comprises three elements, a base part 101, body 102 and cap 103.

As can be seen from FIG. 5, the cap 103 includes ports to provide vacuum and collector electrode connections 130; pressure protection/diffuser exit pressure control 131; 132, access for a glow plug/thermocouple unit 220; hydrogen 133 to the jet nozzle 141; air 134 to support combustion in the flame chamber 120; and access 135 for an HT lead 125. Also provided in the cap are holes 136–139 for fixing bolts, two of which are long to fix the cap to the body and the base, and two of which are short to fix the body to the cap. The ports 130–139 extend through the cap 103 and communicate with connecting bores 130'–139' which extend through the body part 102 (see FIG. 6).

The base 101 on which the body part 102 is located by means of a pair of locating pins 118,118' and to which it is attached by means of long fixing bolts (not shown) extending through the bores 136',137' and into engagement in corresponding bores 116,116' in the base, is provided with an air protect and diffuser pressure control chamber 111 which communicates with a diffuser chamber 110 which surrounds the end of a sampling tube (not shown) which passes through a bore 112 formed in the base. The HT lead 125 connects with an HT electrode 105 which is mounted in a bore 115 in the base 101 and which overlies a ground electrode 104 which is formed in a screw threaded protrusion 106 by means of which the device is mounted in the conventional screw threaded aperture in a cylinder head (not shown).

The body part 101 has, mounted in the bore 130' which forms a flame chamber 120, a mounting block 140 which supports the mixing nozzle 141 to which both hydrogen and the sample gas are fed, the sample gas being fed through a small diameter sampling tube 142 from the diffuser chamber 110. A collector electrode 143 extends into the flame chamber 120 and is supported in a combined collector support and vacuum line connector 144 which is shown in more detail in FIG. 12. The collector electrode 143 is mounted in an insulator block 145 and has a connector terminal 146 by means of which it is connected to the electrical control system (not shown). The electrical control system is preferably the same as that described above and will therefore not be further described. However, for certain high sensitivity applications it may be advantageous to include a signal conditioning unit close to the collector in order to maximise the signal to noise ratio. The combined connector 144 also includes a connecting part 147 for connection of a vacuum line by means of which gases burnt in the flame chamber are removed from the FID.

In order to ignite the hydrogen/sample gas mixture in the flame chamber 120 a combined glow plug/thermocouple unit 220 is provided for insertion in the port 132 and bore 132' in the cap and body parts respectively. The glow plug/thermocouple unit has a narrow diameter thermocouple 221 mounted in an insulating block 222 in turn mounted in a bore in a tubular fitting 223. A platinum wire 224 is spot welded between the end of the thermocouple 221 and the end face of the fitting 223 by means of which a single connection to the thermocouple 221 can provide current for both the glow plug wire 224 and the temperature sensing thermocouple 221. This reduces the number of connections which need to be made and bores which need to be provided in the cap 103 and body 102.

In use, the base 101 is first screwed into the cylinder head and thereafter the body, with the cap mounted on it, is then located on the base 100 and tightened to it by means of the connecting bolts which extend through the ports 136,137 and through corresponding bores (not shown) in the body 102 and into engagement with the bores 116 and 116' in the base 101. Air is provided through the pressure protect port 131 to the vicinity of the diffuser chamber 110 and can be maintained at a sufficiently high pressure to prevent gas entering the device from the combustion chamber in the cylinder head. When the device is required to carry out hydrocarbon detection then the pressure can be reduced accordingly to allow gas to enter and be mixed in the nozzle and injected into the flame chamber for ignition by the glow plug unit 220, the burnt gases subsequently being removed through the vacuum line connector 144,147. In use the diffuser provides substantially constant flow rate sampling into the flame chamber to ensure consistency of measurement. The operation of the FID is described above and will not be described further.

We claim:

1. A flame ionization detector having improved response time to changes in a hydrocarbon sample gas obtained from a sample gas supply, said flame ionization detector comprising:

a housing, said housing defining a flame chamber for burning hydrogen, an oxidant and the sample gas therein;

a nozzle having a base mounted in said housing, said nozzle extending into said chamber and having a tip at which the burning occurs;

inlet means for supplying the hydrogen, the oxidant and the sample gas to said flame chamber, said inlet means for said sample gas comprising conduit means passing along said nozzle and having a first end adjacent said nozzle tip for emitting the sample gas;

means for igniting the sample gas emitted from said sample gas inlet means;

an exhaust outlet through which the products of combustion are removed from said flame chamber;

a collector electrode electrically insulated from said housing, said nozzle and housing being electrically connected together and grounded, said collector electrode being maintained in use, at a predetermined potential relative to ground; and a pre-chamber within said housing and couplable to the sample gas supply, said pre-chamber having a second end of said sample gas inlet conduit means extending therein for receiving sample gas from the supply, said pre-chamber being disposed immediately adjacent said base of said nozzle for minimizing the length of the path the sample gas must travel in said flame ionization detector thereby to improve its response time, said pre-chamber being adapted to maintain a substantially constant static pressure in said sample gas inlet means, whereby the pressure of the sample gas supplied to said nozzle remains substantially constant.

2. A flame ionization detector according to claim 1, wherein said pre-chamber has means couplable to means for applying a controllable pressure to said pre-chamber for controlling the pressure in said pre-chamber and for maintaining the substantially constant static pressure in said sample gas inlet means.

3. A flame ionization detector according to claim 2, wherein said pre-chamber includes a second conduit means couplable to the sample gas supply and extending into said pre-chamber for supplying sample gas thereto, and wherein said second end of said sample gas inlet means is disposed transverse to said second conduit means and in fluid communication therewith, whereby the sample gas enters the second end of said sample gas inlet means substantially at the pre-chamber pressure.

4. A flame ionization detector according to claim 2, wherein said pre-chamber contains a diffuser section having a first end couplable to the sample gas supply and a second end opening into said pre-chamber, said diffuser section diverging in the direction of gas flow therethrough for reducing dynamic pressure variations i the sample gas, said diffuser section having a relatively large open surface area at said second end to enable the maintenance of the substantially constant static pressure.

5. A flame ionization detector according to claim 4, wherein said diffuser section is formed from a plurality of concentric close fitting tubes to provide a stepped, divergent, diffuser means.

6. A method of measuring hydrocarbon concentration in a gas, using a flame ionization detector according to claim 2, wherein, the pressure in the pre-chamber is maintained substantially constant by regulating the pressure in one of the pre-chamber and flame chamber.

7. A method according to claim 6, wherein the pre-chamber is operated at sub-atmospheric pressure by applying a vacuum to said means for applying a controllable pressure to said pre-chamber.

8. A method according to claim 6, wherein the pre-chamber is operated at super-atmospheric pressure.

9. A method according to claim 6, for measuring hydrocarbon concentration in the exhaust gases of an internal combustion engine.

* * * * *